(12) United States Patent
Bartholeyns

(10) Patent No.: US 6,881,413 B1
(45) Date of Patent: Apr. 19, 2005

(54) HUMANIZED BIOMATERIALS, A PROCESS FOR THEIR PREPARATION AND THEIR APPLICATIONS

(75) Inventor: Jacques Bartholeyns, Turquant (FR)

(73) Assignee: I.D.M. Immuno-Designed Molecules, Paris (FR)

( * ) Notice: Subject to any disclaimer, the term of this patent is extended or adjusted under 35 U.S.C. 154(b) by 0 days.

(21) Appl. No.: 10/069,575

(22) PCT Filed: Aug. 22, 2000

(86) PCT No.: PCT/EP00/08157

§ 371 (c)(1),
(2), (4) Date: Jun. 12, 2000

(87) PCT Pub. No.: WO01/15753

PCT Pub. Date: Mar. 8, 2001

(30) Foreign Application Priority Data

Aug. 30, 1999 (EP) .............................. 99402149

(51) Int. Cl.[7] .............................. A61K 9/00; A61F 2/02; C12N 5/08

(52) U.S. Cl. ........................ 424/400; 424/422; 424/423; 435/366; 435/372; 435/375; 435/395

(58) Field of Search ................................. 424/400, 422, 424/423, 93.7; 435/366, 372, 375, 395

(56) References Cited

U.S. PATENT DOCUMENTS

| | | | |
|---|---|---|---|
| 4,485,096 A | | 11/1984 | Bell |
| 4,963,489 A | * | 10/1990 | Naughton et al. ........... 435/1.1 |
| 5,885,829 A | | 3/1999 | Mooney et al. |
| 5,902,741 A | | 5/1999 | Purchio et al. |
| 6,139,578 A | * | 10/2000 | Lee et al. ................ 623/16.11 |

FOREIGN PATENT DOCUMENTS

| | | |
|---|---|---|
| EP | 0 798 374 | 10/1997 |

* cited by examiner

*Primary Examiner*—Leon B. Lankford, Jr.
*Assistant Examiner*—Ruth A. Davis
(74) *Attorney, Agent, or Firm*—Young & Thompson

(57) ABSTRACT

The invention relates to humanized biomaterial comprising a porous biocompatible composite material customized and implanted with monocyte derived cells preferably with macrophages.

4 Claims, No Drawings

HUMANIZED BIOMATERIALS, A PROCESS FOR THEIR PREPARATION AND THEIR APPLICATIONS

The invention relates to new humanized biomaterials, a process for their preparation and their applications.

Tissue repair is needed after severe bone fractures, cartilage loss or general fragilization during ageing.

Artificial metallic or even ceramic prostheses are not very well integrated within host tissues and replacement with new surgery is often required after a few years, a major problem of handicap for old people.

Autologous grafts of bones or cartilage tissue is very difficult and costly. New technologies develop porous matrices implanted as scaffold prosthesis.

These matrices can eventually be filled with growth factors for the tissue regeneration or even with bone marrow stem cells.

However, fixation of cells or factors in the porous matrices with very prolonged and slow release of growth factors is very difficult to achieve and the ideal cocktail and concentration of factors required is unknown.

The aim of the present invention is to provide a homogeneous humanized, bioactive biomaterial (for example porous ceramics) that can be used for implantation purposes and which do not present the long term biocompatibility problems of prior art.

Another aim of the invention is to provide a bioactive biomaterial enabling tissue growth (for example bone and cartilage) in its porous space and securing the integration of the grafted biomaterial in the surrounding tissues (viable bones . . . ).

Another aim of the invention is to provide long lasting prostheses, which avoids requirement for replacement of biomaterial prostheses after 10 years, as often needed up to now.

These aims are achieved by the invention, which consists in humanized biomaterial comprising a porous biocompatible composite material customized and implanted with monocyte derived cells and preferably with macrophages.

The expression "humanized" means that the porous biomaterial has been colonized with human cells derived from blood monocytes.

The expression "biocompatible" composite material designates a material composed of one or several of the following materials proved to be non toxic for human tissues (carbon microfibers, ceramics, calcium phosphates, metal oxides, collagen polymers . . . ).

The expression "porous" means that the biomaterial and preferably the ceramic present pores of about 100 to 2000 microns of diameter.

The expression "customized and implanted" material means that the shape and size of biomaterial is designed specifically for a patient and a site of implantation.

The expression "monocyte derived cells" corresponds to human mononuclear cells isolated from blood, enriched in monocytes and cultured at 37° C. in appropriate medium, for 5 to 10 days to obtain tissue type macrophages.

The monocyte derived cells used in the invention are for instance such as those described in PCT/EP 93/01232, WO 99/13054, EP 96/ 901848.0-2107, WO 97/44441.

In a particular embodiment of the invention, the monocyte derived cells described above, contain exogenous compounds such as drugs, proteins, growth factors of interest.

In another embodiment, the monocyte derived cells as described above contain in their cytoplasm exogenous DNA coding for a protein of interest.

The substantially irreversible humanization of matrices of bio-compatible composite material described in the present invention allows a physiological interaction between the prostheses made of the biomedical composite, grafted and the host cells in the body. These relations with host tissue cells and with the extracellular matrix allow reconstruction of epithelial sheets and growth of a capillary network around the grafted biomaterial by local multiplication and sprouting of endothelial cells.

The monocyte derived cells, in particular the macrophages used to humanize in vitro the porous material in the invention are particularly adequate to increase integration and in vivo lifespan of biocompatible prostheses.

Advantageously, the humanized biomaterial of the invention is homogenous.

According to an advantageous embodiment, in the humanized biomaterial of the invention, the biocompatible composite material is chosen among the following materials: microfibres, ceramic materials, metal oxides such as aluminum oxide, calcium phosphate ceramic, glass or carbon fibers, hydroxylapatite, silicon carbide or nitride, collagen polymers or a mixture of these different materials.

According to another advantageous embodiment, in the humanized biomaterial of the invention, the human macrophages are liable to be obtained by ex vivo differentiation from blood monocytes leading to living macrophages, and are cultured under conditions enabling their penetration and adherence into the biomaterial for instance for several hours at 37° C., with the porous biomaterial, allowing infiltration of the biomaterial and substantially irreversible binding of the living macrophages to the biomaterial, now humanized with patient's macrophages and ready for implantation.

The expression "substantially irreversible binding" means that macrophages are tightly bound by numerous contacts with the material and cannot be detached under physiological conditions.

The invention also relates to a living body-supporting implant, characterized by the fact that it comprises or consists of the humanized biomaterial as described above, and is preferably structured under the form of scaffold, tissue-supporting sponges, bone or cartilage.

A process for the preparation of a humanized biomaterial of the invention comprises the following steps:
  preparation of the porous biomaterial structured in form of bones, cartilage,
  preparation of macrophages from blood monocytes,
  immersion of the biomaterial in a physiologic solution appropriate for the culture of macrophages which are added afterwards (ex.: phosphate buffered saline, medium such as RPMI, IMDM, AIMV),
  addition of the macrophage to the solution under conditions enabling binding to the biomaterial and particularly for 1 to 20 h. at 37° C., 5% CO2 and 95% air,
  washing of the biomaterial and conservation until use in physiologic medium.

A process for the preparation of a living body-supporting implant of the invention comprises the following steps:
  preparation of a customized porous implant or scaffold composed of bio-compatible material, as described above,
  preparation of macrophages from blood monocytes of the patient needing the customized implant of biomaterial,
  co-culture of macrophages and the implant in adequate medium under conditions enabling penetration and adherence to the biomaterial, in particular at 37° C., 5% CO2 in hydrophobic bags or containers until grafting the implant.

The invention also relates to the use of the humanized biomaterial or of a living body-supporting implant, which can be implanted in a tissue, for the in vitro or in vivo or ex vivo delivery of factors chosen in the group of chemokines and/or monokines, and/or cytokines and/or growth factors, the factors released being useful for the local attraction of cells required for tissue growth (such as osteoblasts, chondrocytes, fibroblasts, epithelial cells . . . ) and/or for the neovascularization around the implanted biomaterial, and/or for the release of growth factors sustaining proliferation of cells and/or the growth of new tissues.

Indeed, macrophages maintain tissue homeostasis through the secretion of at least 80 growth factors or monokines controlling and inducing proliferation of mesenchymal (fibroblasts . . . ), endothelial, chondrocytes, osteoblasts, epithelial cells.

They also secrete enzymes and mediators allowing growth and renewal of the surrounding cells and tissues (see Table 1).

The key factors secreted by macrophages supporting tissue integration regeneration and growth of mesenchymal cells are: IGF1 and TGFs, but also PDGF, bFGF, MDGF, GM-CSF, NAF, IL-8, TNF, angiogenin and angiogenic factors. These growth factors allow also the development of all the steps required for angiogenesis, allowing neovascularisation and reconstitution of blood microcapillaries around the grafted biomaterial.

In this aspect, macrophages are synthesizing 10 fold more proteins than monocytes, much more growth factors and less inflammatory mediators.

TABLE 1

GROWTH FACTORS PROTEINS AND MEDIATORS SUPPORTING TISSUE HOMEOSTASICS SECRETED BY NATURE MACROPHAGES

ENZYMES:

Lyzosymes
Neutral proteases
Plasminogen activator
Collagenase
Elastase
Angiotensin-convertase
Acid hydrolases
Proteases
Lipases
Ribonucleases
Phosphatases
Glycosidases
Sulphatases
Arginase
COMPLEMENT COMPONENTS C1, 4, 2, 3 and 5
Factors B and D and Properdin
C1 inhibitor
C3b inactivator and β-1H
ENZYME INHIBITORS (Antiproteases)
α1-antiprotease
Plasmin inhibitors
α-2 macroglobulin
Plasminogen activator inhibitors
PROTEINS BINDING
METABOLIOUS AND LIPIDS:

Acidic isoferritins
Transferrin
Transcobalamin II
Fibronectin
Laminin

TABLE 1-continued

GROWTH FACTORS PROTEINS AND MEDIATORS SUPPORTING TISSUE HOMEOSTASICS SECRETED BY NATURE MACROPHAGES

Lipid transfer protein
Thrombospondin
NUCLEOSIDES AND
METABOLITES:

Thymidine and deoxycytidine
Uracil
Uric acid
Lactic acid
Polyamines nitrines and nitrates
Neopterin
BIOACTIVE LIPIDS:

Arachidonic acid metabolites
Prostaglandins E2, F2α
Prostacyclin
Thromboxane
Leukotrienes B4, C, D and E
Hydroxy-eicosatetraneoic acids
(including SRS-A)
Platelet activating factors
CYTOKINES HORMONES
GROWTH FACTORS:

Interleukens 1 α and β
Tumours necrosis factor α
Interferons α and $β_1$ &
Interleukin 6, 8, 13, 18
Chemotatic factors for
Neutrophils
Tlymphocytes
Monocytes
Fibroblasts
Heamatopocetic Colony Stimulating
Factors for
Granulocyte-Macrophages (GM-CSF)
Granulocytes (G-CSF)
Macrophages (M-CSF)
Erythropoeitin
Growth factors
Fibroblasts growth factor/
Insulin like G.F.
"platgelet-derived growth factor"
(PDGF)
Transforming growth factor α and β
Endothelial cell growth factor
Hormones
1 α, 25-Dihydroxyvitamin D3
Insulin-like activity, protagandins
Thymosin B4
β endorphin
Adrenocorticotrophic hormone
CHEMOKINES MIP/RANTE
FAMILIES COAGULATION
FACTORS:

Factors III, VIII, and tissue factor
Prothrombin and prothrombinase
Factors IX, X, V and VII In an advantageous embodiment of the invention, the macrophages migrate initially in the porous biomaterial and incorporate irreversibly into this prosthesis by very strong adherence and spreading. When they are kept in physiological conditions, macrophages are very long living cells lasting from several months to several years after implantation. During this time, macrophages will continuously secrete growth factors and cytokines in their local environment; these factors will act in synergy at very low concentrations ($10^{-10}$ M) on the surrounding cells and tissues.

Furthermore, macrophages do present on their membranes receptors for cytokines, hormones, sugars allowing to respond to micro-environmental needs and to adjust their secretion to the local status around the biomaterial at different periods after grafting.

The growth factors secreted by macrophages represent the global requirements for tissue repair, differentiation and local angiogenesis. The chemokines which will be continuously released in a concentration gradient around the implant will call in and around the prosthesis cells required for recolonization and integration of the biomaterial in host environment. Therefore, the new customized porous biomaterials colonized with host macrophages present a novel biotolerance and a length of adequate performance far better than prosthesis used in the absence of autologous macrophages. Applications are very large in solid or cartilaginous prosthesis needed in bone, cartilaginous repair particularly.

According to another advantageous embodiment, the invention relates to the use of the humanized biomaterial or of a living body-supporting implant, as a graft for the replacement of supporting tissues such as bones, cartilages, dental tissues, epithelial sheet and subcutaneous tissue matrix.

EXAMPLE 1

A calcium phosphate porous ceramic with pores of 200 to 2000 microns (porosity>20% and <80%) is placed on an hydrophobic support (ethylene vinyl acetate) in the presence of 50 ml AIMV culture medium (life-cell Gibco, Paisley G. B.). Macrophages are added to this preparation at the concentration of $5.10^6$ cells/ml; they are obtained after 7 days differentiation of blood monocytes in culture according to published state of the art in publications and patents (PCT/EP 93/01232, WO 99/13054, EP 96/ 901848.0-2107, WO 97/44441); a control preparation is maintained in the absence of macrophages. The preparation is incubated overnight at 37° C., 5. % $CO_2$, 95% air to allow fixation of macrophages on the ceramic.

The porous ceramic is washed and cultured in the presence of fibroblasts and/or in the presence of chondrocytes. In both cases, the cell proliferation is higher by a factor 2 to 10 for the porous ceramic colonized with macrophages, compared to control ceramic.

EXAMPLE 2

A small fragment of porous microceramic is implanted in a rabbit cornea. The inert microceramic piece induces a very small to moderate inflammation and only peripheral growth of new blood vessels from the ring of the cornea.

In contrast, microceramic covered with macrophages, as described in example 1 induces a major neovascularisation towards the center of the cornea. The cornea becomes vascularized through an invasion of endothelial cells arising from the rim rich in blood supply and sprouting towards the biomaterial implanted.

EXAMPLE 3

Fragments of 100+/−20 mg of hydroxyapatite ceramic (Endobon®, Merck) and pieces of one cm2 of a polypropylene scaffold are prepared. Fresh non activated macrophages obtained after 7 days differentiation of blood monocytes in culture according to published patent applications (WO94/26875, WO 99/13054, WO96/22781, WO 97/44441) are suspended ($2,5.10^6$ cells/ml) in IMDM (Iscove Modified Dulbecco Medium) culture medium. Each biomaterial fragment is incubated in 1 ml of macrophage suspension, in sterile polypropylene tubes, for 4 hours at room temperature. To check the binding of macrophages on the biomaterial, cells present in the supernatant after incubation are counted. After incubation with Endobon®, from 12 to 17% of the cells added were present in the supernatant (3 experiments), indicating that more than $2.10^6$ macrophages are adsorbed on 100 mg of porous ceramic. After incubation with polypropylene scaffold, from 23 to 55% of the cells initially added are present in the supernatant, indicating adsorption of 1 to $2.10^6$ macrophages/cm2 scaffold.

Nude mice are implanted with biomaterial, and each mouse receives two implants of the same type, one in each flank.

| Mice n° | Implanted material |
|---------|-------------------|
| 1, 2    | Endobon® colonized by macrophages |
| 3       | Endobon® |
| 4, 5    | Polypropylene colonized by macrophages |
| 6       | Polypropylene |

Mice are sacrificed after 21 days, macroscopic observation shows no major difference between implants of biomaterial alone and implants of biomaterial colonized by macrophages.

Microscopic observation of tissues in paraffin shows that, when compared to implants of biomaterial alone, implants of biomaterial colonized by macrophages induce first an inflammation phenomenon, which is an important step to induce migration and homing of competent cells for tissue repair. A more important neovascularisation at the implantation site of biomaterial colonized with macrophages has also been observed.

The histological analysis of tissues in resin confirms the increase of neovascularisation for mice implanted with macrophages colonized biomaterials when compared to mice implanted only with biomaterial.

The therapeutic applications for tissue repair are confirmed in human bearing non healing ulcers. The ulcers covered with scaffold implanted with autologous macrophages show an improved cicatrization as measured by detersion and size of the ulcer.

What is claimed is:

1. A humanized biomaterial ready for implantation comprising a porous bio-compatible composite material that is customized and implanted with living monocyte derived cells substantially irreversibly bound to said porous biocompatible composite material, wherein said monocyte derived cells are macrophages which have been obtained by ex vivo differentiation of blood monocytes taken from a human patient and wherein the living macrophages are cultured under conditions such that when implanted into the porous biocompatible composite material the macrophages penetrate and substantially irreversibly bind to said porous biocompatible composite material.

2. The humanized biomaterial according to claim 1, wherein the biocompatible composite material is selected from the group consisting of microfibers, ceramic materials, metal oxides, calcium phosphate ceramic, glass fibers, carbon fibers, hydroxylapatite, silicon carbide, silicon nitride, collagen polymers and a mixture of these different materials.

3. The humanized biomaterial according to claim 2, wherein said biocompatible material is aluminum oxide.

4. An implant comprising the humanized biomaterial according to claim 1, and wherein said implant is structured in a form selected from the group consisting of scaffold, tissue-supporting sponges, bone and cartilage.

* * * * *